United States Patent
Sharabani et al.

(10) Patent No.: US 9,820,865 B2
(45) Date of Patent: Nov. 21, 2017

(54) ADJUSTABLE IMPLANT

(71) Applicant: NLT SPINE LTD., Kfar Saba (IL)

(72) Inventors: Netanel Sharabani, Rishpon (IL); Oded Loebl, Tel Mond (IL); Didier Toubia, Raanana (IL)

(73) Assignee: NLT SPINE LTD., Kfar Saba (IL)

( * ) Notice: Subject to any disclaimer, the term of this patent is extended or adjusted under 35 U.S.C. 154(b) by 0 days.

(21) Appl. No.: 15/028,427

(22) PCT Filed: Oct. 30, 2014

(86) PCT No.: PCT/IB2014/065718
§ 371 (c)(1),
(2) Date: Apr. 10, 2016

(87) PCT Pub. No.: WO2015/063721
PCT Pub. Date: May 7, 2015

(65) Prior Publication Data
US 2016/0250034 A1  Sep. 1, 2016

Related U.S. Application Data

(60) Provisional application No. 61/897,989, filed on Oct. 31, 2013.

(51) Int. Cl.
*A61F 2/44* (2006.01)
*A61F 2/46* (2006.01)
(Continued)

(52) U.S. Cl.
CPC .............. *A61F 2/4425* (2013.01); *A61F 2/44* (2013.01); *A61F 2/447* (2013.01); *A61F 2/4611* (2013.01);
(Continued)

(58) Field of Classification Search
CPC .......... A61F 2/4425; A61F 2/44; A61F 2/447; A61F 2/4611; A61F 2002/2817;
(Continued)

(56) References Cited

U.S. PATENT DOCUMENTS

| 4,759,769 A | 7/1988 | Hedman et al. |
|---|---|---|
| 5,059,193 A | 10/1991 | Kuslich |

(Continued)

FOREIGN PATENT DOCUMENTS

| DE | 2263842 | 7/1974 |
|---|---|---|
| DE | 9107494 | 9/1991 |

(Continued)

OTHER PUBLICATIONS

E. AliCl, et al "Prostheses Designed for Vertebral Body Replacement" in Journal of Biomechanics vol. 23 1990, No. 8. pp. 799-809.

*Primary Examiner* — Pedro Philogene
*Assistant Examiner* — David C Comstock
(74) *Attorney, Agent, or Firm* — Mark M. Friedman

(57) ABSTRACT

An adjustable implant (10, 60, 70, 80, 90) has a base (12) and a displaceable element (16) providing opposing tissue contact surfaces (14, 18). A linkage (20, 26) is pivotally connected to the displaceable element. A linkage mover (38, 40), engaged so as to be displaceable along the base, is associated with the linkage (20, 26) so as to define a displaceable pivot location (24, 30) for pivotal motion of the linkage relative to the base, in certain preferred embodiments, the base (12) has an internally threaded track (42, 44) in which a threaded segment of the linkage mover (38, 40) is engaged, so that rotation of the threaded segment about its central axis advances the linkage mover along the threaded track, thereby displacing the displaceable pivot locations and adjusting a separation between the first contact surface and at least part of the second contact surface.

16 Claims, 11 Drawing Sheets

(51) Int. Cl.
    *A61F 2/30* (2006.01)
    *A61F 2/28* (2006.01)
    *A61B 17/88* (2006.01)

(52) U.S. Cl.
    CPC ... *A61B 17/8852* (2013.01); *A61F 2002/2817* (2013.01); *A61F 2002/2835* (2013.01); *A61F 2002/30405* (2013.01); *A61F 2002/30415* (2013.01); *A61F 2002/30418* (2013.01); *A61F 2002/30471* (2013.01); *A61F 2002/30538* (2013.01); *A61F 2002/30542* (2013.01); *A61F 2002/30556* (2013.01); *A61F 2002/30579* (2013.01); *A61F 2002/30601* (2013.01); *A61F 2002/30629* (2013.01); *A61F 2002/30632* (2013.01); *A61F 2002/30637* (2013.01); *A61F 2002/30827* (2013.01); *A61F 2002/30904* (2013.01); *A61F 2002/30912* (2013.01); *A61F 2002/4475* (2013.01); *A61F 2002/4627* (2013.01)

(58) Field of Classification Search
    CPC .... A61F 2002/2835; A61F 2002/30405; A61F 2002/30418; A61F 2002/30471; A61F 2002/30538; A61F 2002/30542; A61F 2002/30556; A61F 2002/30579; A61F 2002/30601; A61F 2002/30629; A61F 2002/30632; A61F 2002/30637; A61F 2002/30827; A61F 2002/30904; A61F 2002/30912; A61F 2002/4475; A61F 2002/4627; A61B 17/8852
    USPC .................. 606/246; 623/17.15, 17.16, 23.47
    See application file for complete search history.

(56) References Cited

U.S. PATENT DOCUMENTS

| | | |
|---|---|---|
| 5,171,278 A | 12/1992 | Pisharodi |
| 5,258,031 A | 11/1993 | Salib et al. |
| 5,390,683 A | 2/1995 | Pisharodi |
| 5,534,029 A | 7/1996 | Shima |
| 5,599,279 A | 2/1997 | Slotman |
| 5,620,458 A | 4/1997 | Green et al. |
| 6,039,761 A | 3/2000 | Li et al. |
| 6,080,193 A | 6/2000 | Hochshuler et al. |
| 6,126,689 A | 10/2000 | Bret |
| 6,190,414 B1 | 2/2001 | Young et al. |
| 6,193,757 B1 | 2/2001 | Foley |
| 6,238,403 B1 | 5/2001 | Greene, Jr. et al. |
| 6,332,894 B1 | 12/2001 | Stalcup et al. |
| 6,368,351 B1 | 4/2002 | Glenn |
| 6,375,682 B1 | 4/2002 | Fleischmann et al. |
| 6,387,130 B1 | 5/2002 | Stone et al. |
| 6,419,705 B1 | 7/2002 | Erickson |
| 6,443,989 B1 | 9/2002 | Jackson |
| 6,491,724 B1 | 12/2002 | Ferree |
| 6,576,016 B1 | 6/2003 | Hochshuler et al. |
| 6,582,451 B1 | 6/2003 | Marucci et al. |
| 6,620,196 B1 | 9/2003 | Trieu |
| 6,641,614 B1 | 11/2003 | Wagner et al. |
| 6,676,665 B2 | 1/2004 | Foley et al. |
| 6,706,070 B1 | 3/2004 | Wagner et al. |
| 6,830,589 B2 | 12/2004 | Erickson |
| 7,070,598 B2 | 7/2006 | Lim et al. |
| 7,087,055 B2 | 8/2006 | Lim et al. |
| 7,097,648 B1 | 8/2006 | Globerman et al. |
| 7,431,735 B2 | 10/2008 | Liu et al. |
| 7,621,956 B2 | 11/2009 | Paul |
| 7,625,377 B2 | 12/2009 | Veldhuizen et al. |
| 7,641,690 B2 | 1/2010 | Abdoiu |
| 7,655,046 B2 | 2/2010 | Dryer et al. |
| 7,720,282 B2 | 5/2010 | Blake et al. |
| 7,763,028 B2 | 7/2010 | Lim et al. |
| 7,799,081 B2 | 9/2010 | McKinley |
| 7,846,206 B2 | 12/2010 | Oglaza et al. |
| 7,850,734 B2 | 12/2010 | Oh |
| 7,901,409 B2 | 3/2011 | Canaveral et al. |
| 7,905,920 B2 | 3/2011 | Galea |
| 7,909,872 B2 | 3/2011 | Zipnick et al. |
| 7,938,860 B2 | 5/2011 | Trieu |
| 7,947,078 B2 | 5/2011 | Siegal |
| 7,959,652 B2 | 6/2011 | Zucherman et al. |
| 8,021,429 B2 | 9/2011 | Viker |
| 8,025,665 B2 | 9/2011 | Lim et al. |
| 8,062,375 B2 | 11/2011 | Glerum et al. |
| 8,123,809 B2 | 2/2012 | Melkent et al. |
| 8,133,232 B2 | 3/2012 | Levy et al. |
| 8,187,332 B2 | 5/2012 | Mcluen |
| 8,241,331 B2 * | 8/2012 | Arnin ................... A61B 17/025 606/248 |
| 8,292,963 B2 | 10/2012 | Miller et al. |
| 8,303,658 B2 | 11/2012 | Peterman |
| 8,308,802 B2 | 11/2012 | Rhoda et al. |
| 8,317,798 B2 | 11/2012 | Lim et al. |
| 8,317,802 B1 | 11/2012 | Manzi et al. |
| 8,317,866 B2 | 11/2012 | Palmatier et al. |
| 8,323,344 B2 | 12/2012 | Galeey et al. |
| 8,337,531 B2 | 12/2012 | Johnson et al. |
| 8,337,559 B2 | 12/2012 | Hansell et al. |
| 8,343,193 B2 | 1/2013 | Johnson et al. |
| 8,349,013 B2 | 1/2013 | Zucherman et al. |
| 8,349,014 B2 | 1/2013 | Barreiro et al. |
| 8,377,071 B2 | 2/2013 | Lim et al. |
| 8,398,713 B2 | 3/2013 | Weiman |
| 8,403,990 B2 | 3/2013 | Dryer et al. |
| 8,444,697 B1 | 5/2013 | Butler et al. |
| 8,518,120 B2 | 8/2013 | Glerum et al. |
| 8,523,944 B2 | 9/2013 | Jimenez et al. |
| 8,556,979 B2 | 10/2013 | Glerum et al. |
| 8,579,907 B2 | 11/2013 | Lim et al. |
| 8,628,576 B2 | 1/2014 | Triplett et al. |
| 8,628,577 B1 | 1/2014 | Jimenez |
| 8,679,183 B2 | 3/2014 | Glerum et al. |
| 8,685,098 B2 | 4/2014 | Glerum et al. |
| 8,709,086 B2 | 4/2014 | Glerum |
| 8,771,360 B2 | 7/2014 | Jimenez et al. |
| 8,870,959 B2 | 10/2014 | Arnin |
| 9,005,291 B2 | 4/2015 | Loebl |
| 9,017,413 B2 | 4/2015 | Siegal |
| 2002/0026197 A1 | 2/2002 | Foley et al. |
| 2002/0151976 A1 | 10/2002 | Foley |
| 2003/0236520 A1 | 12/2003 | Lim et al. |
| 2004/0059418 A1 | 3/2004 | Mckay et al. |
| 2004/0133280 A1 | 7/2004 | Trieu |
| 2004/0162618 A1 | 8/2004 | Mujwid et al. |
| 2004/0193158 A1 | 9/2004 | Lim et al. |
| 2005/0033431 A1 | 2/2005 | Gordon et al. |
| 2005/0060036 A1 | 3/2005 | Schultz |
| 2005/0113920 A1 | 5/2005 | Foley et al. |
| 2005/0125062 A1 | 6/2005 | Biedermann et al. |
| 2005/0143827 A1 | 6/2005 | Globerman et al. |
| 2005/0182416 A1 | 8/2005 | Lim et al. |
| 2005/0209698 A1 | 9/2005 | Gordon |
| 2005/0228391 A1 | 10/2005 | Levy et al. |
| 2005/0261683 A1 | 11/2005 | Veldhuizen et al. |
| 2005/0278036 A1 | 12/2005 | Leonard et al. |
| 2006/0004455 A1 | 1/2006 | Leonard et al. |
| 2006/0041258 A1 | 2/2006 | Galea |
| 2006/0085070 A1 | 4/2006 | Kim |
| 2006/0142858 A1 | 6/2006 | Colleran et al. |
| 2006/0224241 A1 | 10/2006 | Butler et al. |
| 2006/0235423 A1 | 10/2006 | Cantu |
| 2006/0247778 A1 | 11/2006 | Ferree |
| 2007/0032791 A1 | 2/2007 | Greenhalgh |
| 2007/0073398 A1 | 3/2007 | Fabian et al. |
| 2007/0123986 A1 | 5/2007 | Schaller |
| 2007/0173939 A1 | 7/2007 | Kim et al. |
| 2007/0233245 A1 | 10/2007 | Trieu |
| 2007/0260314 A1 | 11/2007 | Biyani |
| 2007/0282449 A1 | 12/2007 | de Villiers |
| 2008/0119853 A1 | 5/2008 | Felt et al. |
| 2008/0125865 A1 | 5/2008 | Abdelgany |

(56) References Cited

U.S. PATENT DOCUMENTS

| | | |
|---|---|---|
| 2008/0243255 A1 | 10/2008 | Butler et al. |
| 2008/0249628 A1 | 10/2008 | Altarac |
| 2008/0312743 A1 | 12/2008 | Vila et al. |
| 2009/0093882 A1 | 4/2009 | Oh |
| 2009/0157186 A1 | 6/2009 | Magerl |
| 2009/0216274 A1 | 8/2009 | Morancy-Meister et al. |
| 2009/0270873 A1 | 10/2009 | Fabian |
| 2009/0299478 A1 | 12/2009 | Carls et al. |
| 2010/0131009 A1 | 5/2010 | Roebling et al. |
| 2010/0194753 A1 | 8/2010 | Robotham et al. |
| 2010/0211176 A1 | 8/2010 | Greenhalgh |
| 2010/0256764 A1 | 10/2010 | Tsuang et al. |
| 2010/0286787 A1 | 11/2010 | Villiers et al. |
| 2011/0054537 A1 | 3/2011 | Miller |
| 2011/0125270 A1 | 5/2011 | Paul |
| 2011/0276141 A1 | 11/2011 | Caratsch |
| 2012/0004732 A1 | 1/2012 | Joel |
| 2012/0029518 A1 | 2/2012 | Blackwell et al. |
| 2012/0053642 A1 | 3/2012 | Lozier |
| 2012/0083888 A1 | 4/2012 | Moumene et al. |
| 2012/0123546 A1 | 5/2012 | Medina |
| 2012/0165944 A1 | 6/2012 | McGuckin, Jr. |
| 2012/0259416 A1 | 10/2012 | Blackwell |
| 2012/0271422 A1 | 10/2012 | Miller et al. |
| 2012/0277866 A1 | 11/2012 | Kalluri et al. |
| 2013/0041471 A1 | 2/2013 | Siegal et al. |
| 2013/0066374 A1 | 3/2013 | Galley et al. |
| 2013/0079883 A1 | 3/2013 | Butler et al. |
| 2013/0158664 A1 | 6/2013 | Palmatier |
| 2013/0158669 A1 | 6/2013 | Sungarian et al. |
| 2013/0190876 A1 | 7/2013 | Drochner |
| 2013/0197642 A1* | 8/2013 | Ernst .................... A61F 2/4465 623/17.16 |
| 2013/0274883 A1 | 10/2013 | Mcluen et al. |
| 2013/0317615 A1 | 11/2013 | Jimenez et al. |
| 2013/0325128 A1 | 12/2013 | Perloff et al. |
| 2014/0052254 A1 | 2/2014 | Glerum et al. |
| 2014/0114429 A1 | 4/2014 | Slone et al. |
| 2014/0156007 A1 | 6/2014 | Pabst et al. |
| 2014/0188224 A1 | 7/2014 | Dmuschewsky |
| 2014/0188225 A1 | 7/2014 | Dmuschewsky |
| 2014/0243982 A1 | 8/2014 | Miller |
| 2014/0249628 A1 | 9/2014 | Weiman |
| 2014/0249629 A1 | 9/2014 | Moskowitz et al. |
| 2014/0277139 A1 | 9/2014 | Vrionis |

FOREIGN PATENT DOCUMENTS

| | | |
|---|---|---|
| DE | 4416605 | 6/1995 |
| FR | 2717068 | 9/1995 |
| WO | 98/34552 | 8/1998 |
| WO | 03003951 | 1/2003 |
| WO | 03005276 | 1/2003 |
| WO | 2003003951 | 1/2003 |
| WO | 2006050500 | 5/2006 |
| WO | 2006060500 | 5/2006 |
| WO | 2007073584 | 2/2007 |
| WO | 2008044057 | 4/2008 |
| WO | 2008084479 | 7/2008 |
| WO | 2008103781 | 8/2008 |
| WO | 2012117312 | 9/2012 |
| WO | 2013052807 | 4/2013 |
| WO | 2013/133729 | 9/2013 |
| WO | 2013133729 | 9/2013 |
| WO | 2013158294 | 10/2013 |
| WO | 2014091029 | 6/2014 |

* cited by examiner

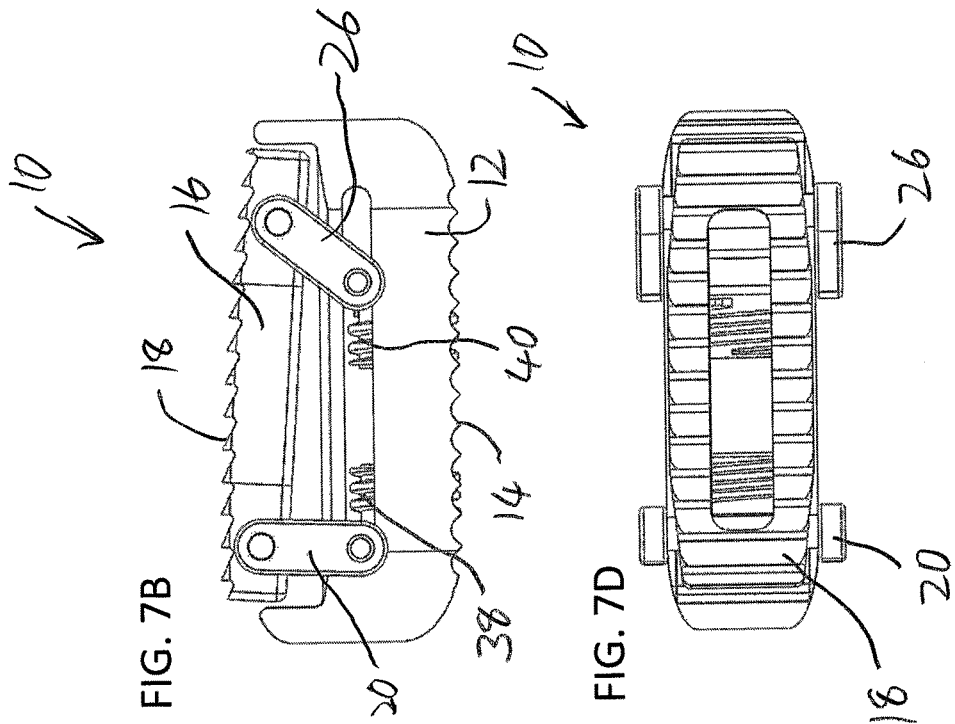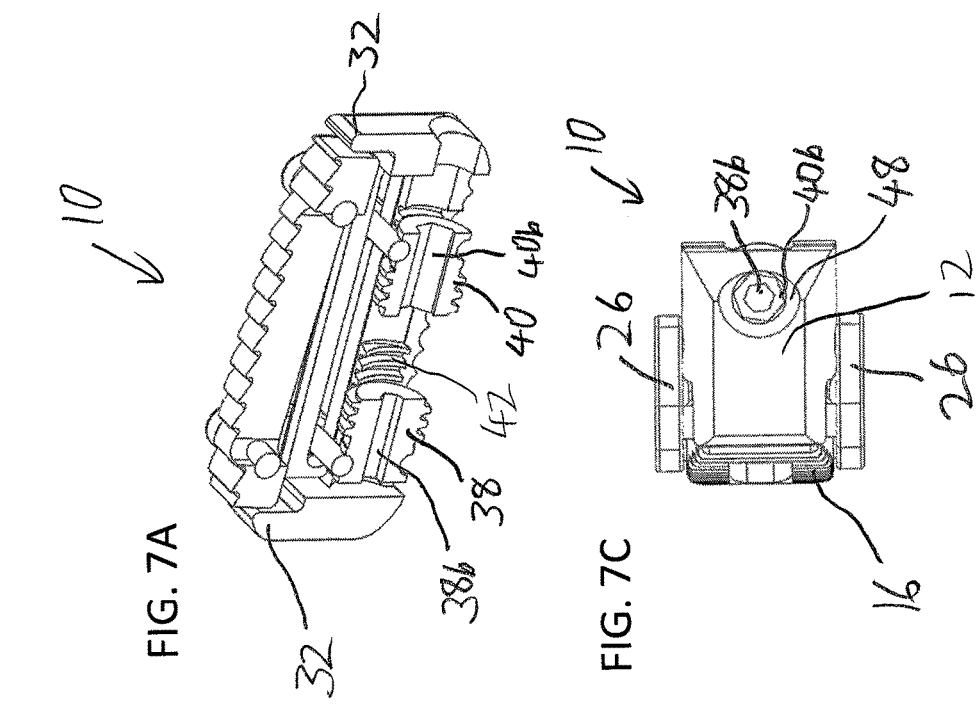

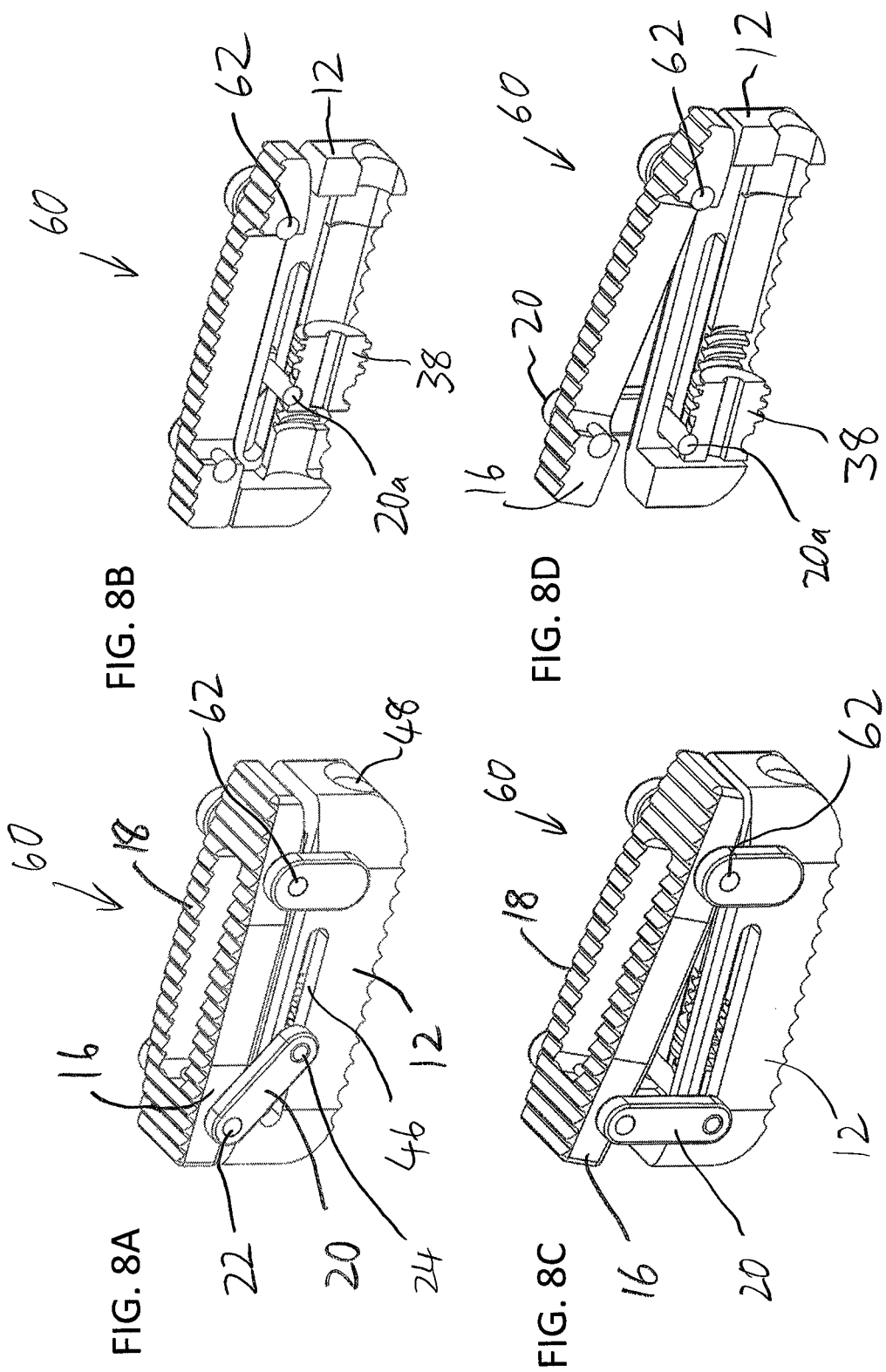

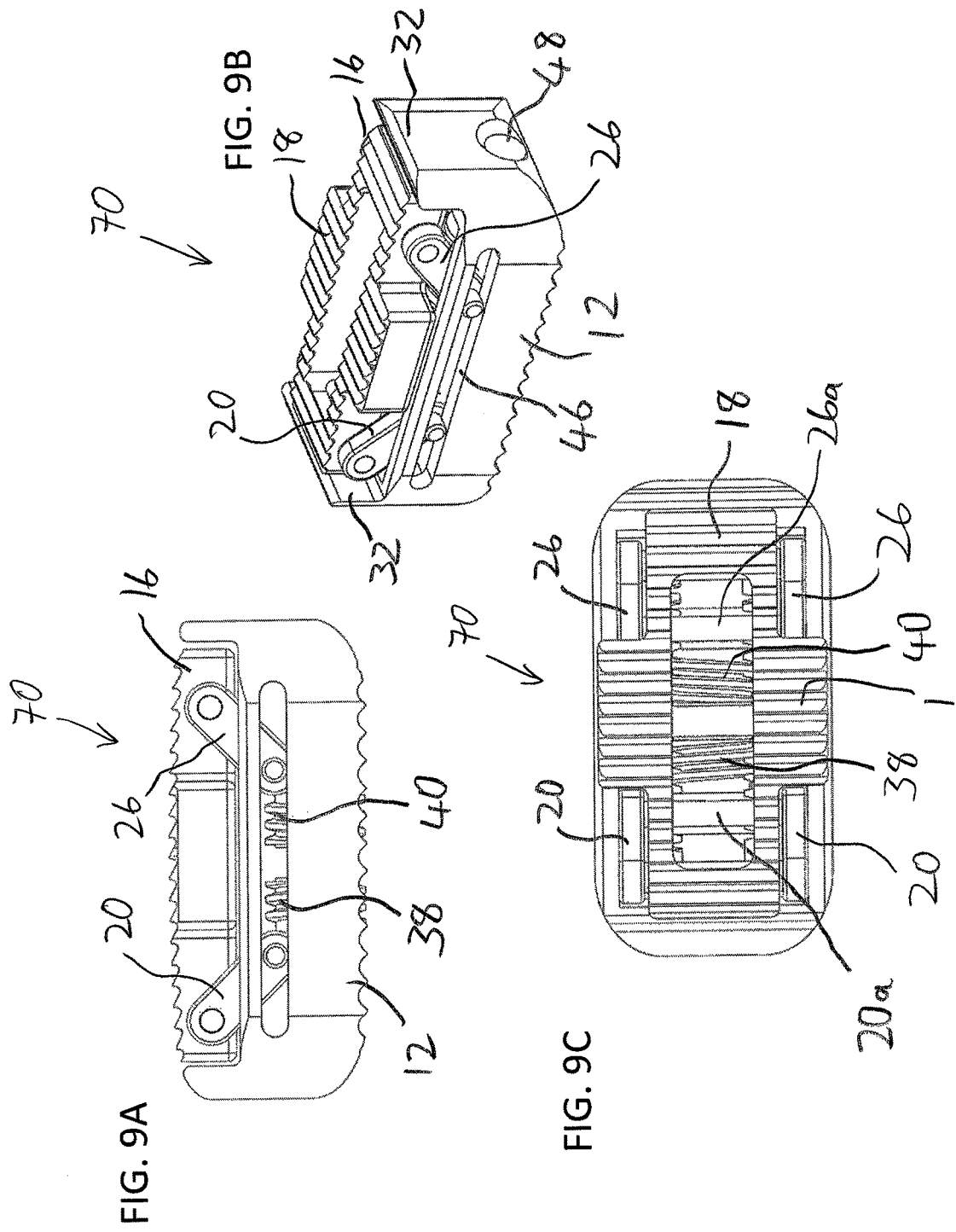

ADJUSTABLE IMPLANT

FIELD AND BACKGROUND OF THE INVENTION

The present invention relates to orthopedic implants and, in particular, it concerns adjustable implants which provide adjustment of either or both a spacing and a relative angle between two tissue contact surfaces.

It is known to provide adjustable implants of various types, such as expanding cages for intervertebral fusion.

SUMMARY OF THE INVENTION

The present invention is an adjustable implant which provide adjustment of either or both a spacing and a relative angle between two tissue contact surfaces.

According to the teachings of the present invention there is provided, an adjustable implant for deployment between a first and a second tissue surface, the implant comprising: (a) a base having a length, the base providing a first contact surface for deployment against the first tissue surface; (b) a displaceable element providing a second contact surface for deployment against the second tissue surface; (c) a linkage pivotally connected to the displaceable element; and (d) a linkage mover engaged with the base so as to be displaceable along at least part of the length of the base, the linkage mover being associated with the linkage so as to define a displaceable pivot location for pivotal motion of the linkage relative to the base, wherein the base comprises an internally threaded track, and wherein the linkage mover comprises a threaded segment engaged with the internally threaded track such that rotation of the threaded segment about a central axis of the threaded segment advances the linkage mover along the threaded track, thereby displacing the displaceable pivot location such that the linkage adjusts a separation between the first contact surface and at least part of the second contact surface.

According to a further feature of an embodiment of the present invention, the linkage mover further comprises an annular groove circumscribing the central axis, and wherein the linkage comprises a pivot pin engaged in the annular groove so as to at least partially define the displaceable pivot location.

According to a further feature of an embodiment of the present invention, the base further comprises a slot extending parallel to the length, and wherein the pivot pin is slidingly engaged in the slot.

According to a further feature of an embodiment of the present invention, the linkage mover further comprises a central non-circular opening, and wherein the base has an opening for insertion of an actuator rod having a key configuration for engaging the non-circular opening so as to allow rotation of the linkage mover so as to adjust the implant.

According to a further feature of an embodiment of the present invention, the displaceable element is pivotally connected to the base such that displacement of the linkage mover results in a change of angle of the second contact surface relative to the first contact surface.

According to a further feature of an embodiment of the present invention, the linkage is a first linkage and the linkage mover is a first linkage mover, the adjustable implant further comprising: (a) a second linkage pivotally connected to the displaceable element; and (b) a second linkage mover engaged with the base so as to be displaceable along part of the length of the base, the second linkage mover being associated with the second linkage so as to define a displaceable pivot location for pivotal motion of the second linkage relative to the base.

According to a further feature of an embodiment of the present invention, the internally threaded track is a first internally threaded track extending along only part of the length, and wherein the base further comprises a second internally threaded track extending along a second part of the length, the second linkage mover comprising a threaded segment engaged with the second internally threaded track, the first and second internally threaded tracks having opposite thread directions.

According to a further feature of an embodiment of the present invention, there is also provided an elongated actuator rod rotationally engaged with both the threaded segments of both the first and second linkage movers such that rotation of the elongated actuator rod is effective to displace the displaceable pivot locations of the first and second linkages in opposing directions.

According to a further feature of an embodiment of the present invention, there is also provided: (a) an actuator rod passing through the threaded segment of the second linkage mover and rotationally engaged with the threaded segment of the first linkage mover; and (b) an actuator tube deployed around the actuator rod, the actuator tube being rotationally engaged with the threaded segment of the second linkage mover.

According to a further feature of an embodiment of the present invention, the first and second linkages are deployed such that increasing a spacing between the first and second displaceable pivot locations is effective to increase a spacing between the first and second contact surfaces.

According to a further feature of an embodiment of the present invention, the base and the displaceable element are formed with interlocking features deployed to limit motion of the displaceable element relative to the base in a direction parallel to the length while allowing a range of spacing between the first and second contact surfaces.

There is also provided according to the teachings of an embodiment of the present invention, an adjustable implant for deployment between a first and a second tissue surface, the implant comprising: (a) a base having a length, the base providing a first contact surface for deployment against the first tissue surface; (b) a displaceable element providing a second contact surface for deployment against the second tissue surface; (c) a first linkage pivotally connected to the displaceable element and pivotally associated with the base at a first displaceable pivot location; (d) a second linkage pivotally connected to the displaceable element and pivotally associated with the base at a second displaceable pivot location; and (e) an actuation arrangement associated with the base and operable to act on the first and second linkages so as to move the displaceable pivot locations, thereby adjusting a spacing and/or angle between the first and second contact surfaces, the actuation arrangement being selectively operable to adjust the first displaceable pivot location without moving the second displaceable pivot location.

According to a further feature of an embodiment of the present invention, the first and second linkages are deployed such that increasing a spacing between the first and second displaceable pivot locations is effective to increase a spacing between the first and second contact surfaces.

According to a further feature of an embodiment of the present invention, the actuation arrangement is a threaded actuation arrangement comprising: (a) an actuator rod mechanically associated with the first linkage such that rotation of the actuator rod displaces the first displaceable pivot location; and (b) an actuator tube deployed around the actuator rod, the actuator tube being mechanically associated with the second linkage such that rotation of the actuator tube displaces the second displaceable pivot location.

According to a further feature of an embodiment of the present invention, the threaded actuation arrangement is configured such that rotation of the actuator rod and the actuator tube in the same direction results in opposing displacements of the first and second displaceable pivot locations.

According to a further feature of an embodiment of the present invention, the base and the displaceable element are formed with interlocking features deployed to limit motion of the displaceable element relative to the base in a direction parallel to the length while allowing a range of spacing between the first and second contact surfaces.

BRIEF DESCRIPTION OF THE DRAWINGS

The invention is herein described, by way of example only, with reference to the accompanying drawings, wherein:

FIGS. 7A, 7B, 7C and 7D are cutaway isometric, side, front and top views, respectively, of the implant in the state of FIG. 4A after removal of the adjustment tool;

FIGS. 8A and 8B are isometric and cutaway (along a center-plane of the implant) views, respectively, of an embodiment of an implant according to the present invention that provides adjustment of the relative angle of the tissue contact surfaces, the implant shown in a flat configuration;

FIGS. 8C and 8D are views similar to FIGS. 8A and 8B, respectively, showing the implant with the tissue contact surfaces angled;

FIGS. 9A-9C are side, isometric and top views, respectively, of a variant of the implant of FIG. 1A-4C where the side linkages are internal to the outer surfaces of the base;

FIGS. 11C and 11B are side views of the implant of FIG. 10A, located on a vertebral endplate in a minimum size and horizontally expanded state, respectively.

DESCRIPTION OF THE PREFERRED EMBODIMENTS

Figure 1A:
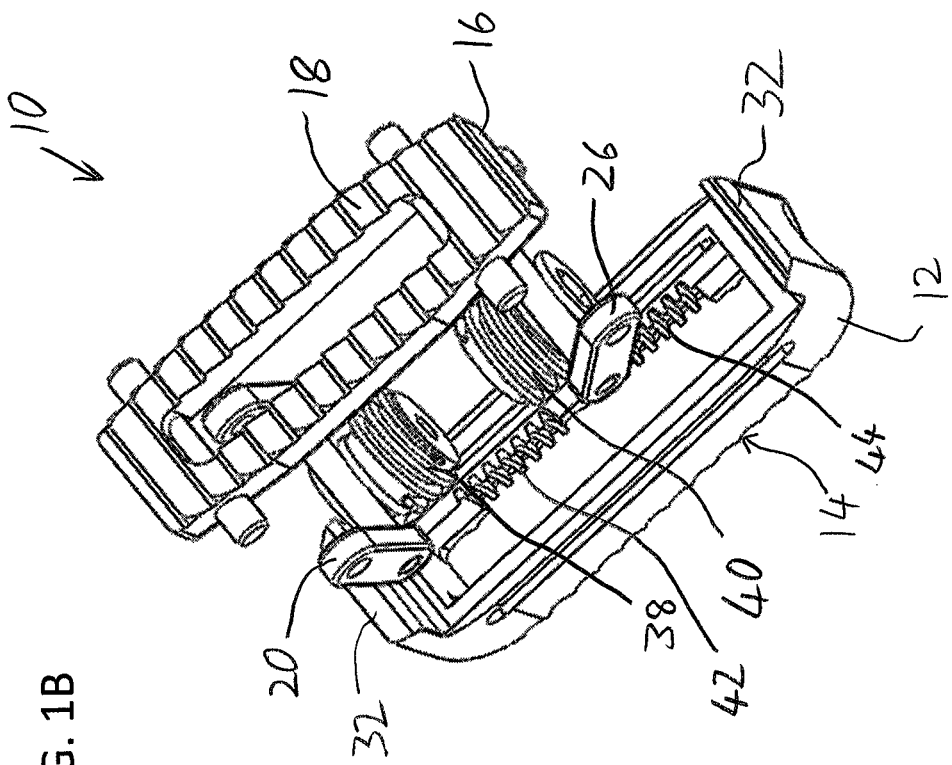
FIGS. 1A-1B are exploded isometric views of an implant illustrating the components according to an embodiment of the present invention.
Figure 1B:
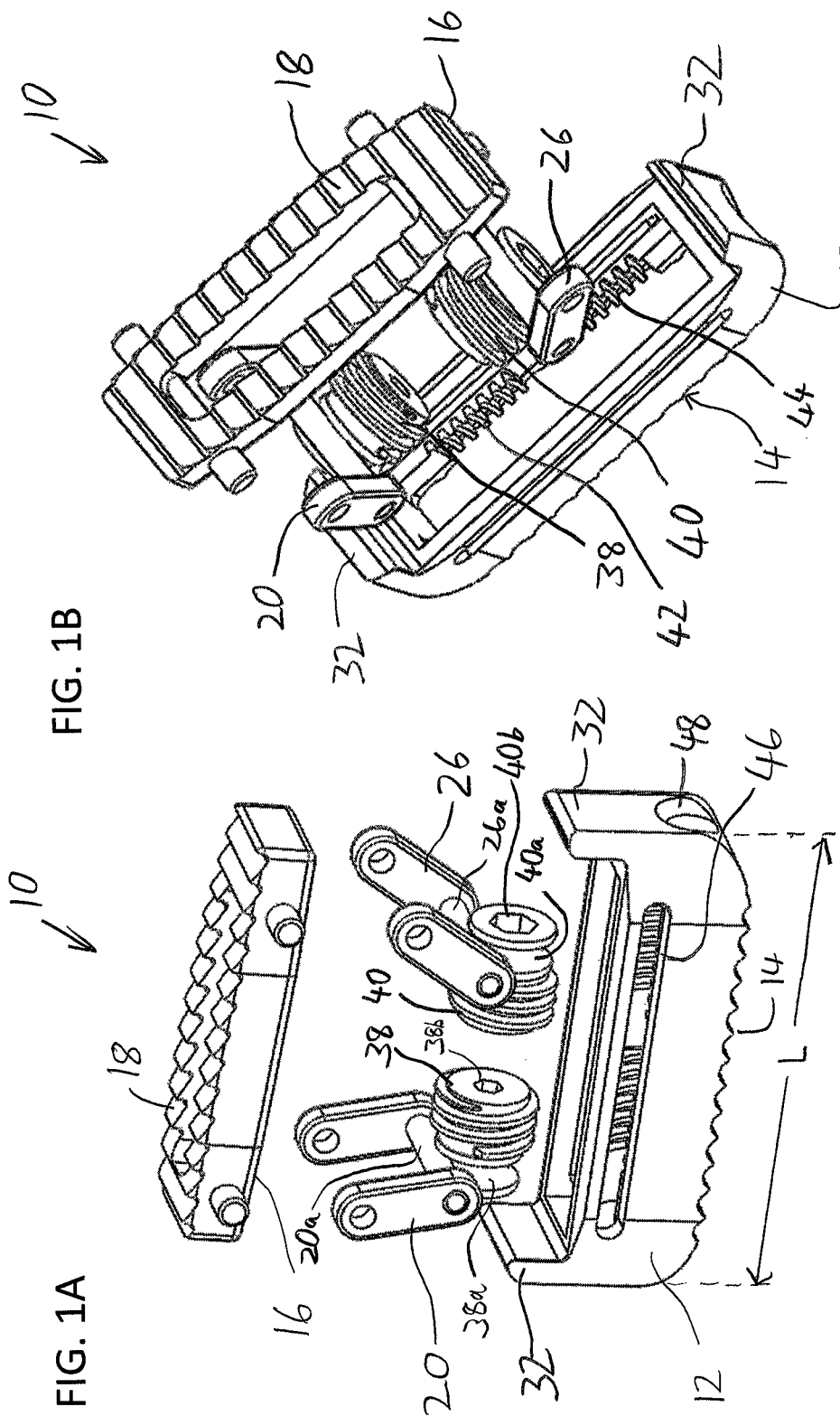

The present invention is an adjustable implant which provide adjustment of either or both a spacing and a relative angle between two tissue contact surfaces.

The principles and operation of implants according to the present invention may be better understood with reference to the drawings and the accompanying description.

By way of introduction, the present invention relates to a group of adjustable orthopedic implants applicable to a wide range of applications. The implants may be used to advantage, with minor adaptations that will be clear to a person having ordinary skill in the art, for a range of applications including, but not limited to: intervertebral fusion with intervertebral height restoration, lordotic correction and/or scoliosis correction; correction of vertebral compression fractures; corpectomy; and other spinal and non-spinal orthopedic applications. Additionally, although illustrated herein in embodiments formed as an elongated straight implant with a length greater than both a width and height of the implant, implants with other shapes and proportions also fall within the scope of the present invention, including but not limited to, wide implants with a width similar to or greater than their length, and implants with curved or "banana-shaped" upper and/or lower contact surfaces.

Referring now to the drawings, FIGS. 1A-7D illustrate various aspects of a first embodiment of an adjustable implant, generally designated 10, constructed and operative according to certain aspects of the present invention, for deployment between a first and a second tissue surface.

Generally speaking, adjustable implant 10 includes a base 12 having a length L, and providing a first contact surface 14 for deployment against the first tissue surface. A displaceable element 16 provides a second contact surface 18 for deployment against the second tissue surface. Contact surfaces 14 and 18 are generally opposing, outward-facing surfaces.

In the embodiment shown here, displaceable element 16 is supported and moved, relative to base 12 by a pair of linkages. A first linkage 20 is pivotally connected to displaceable element 16 at a pivot joint 22 and pivotally associated with the base at a first displaceable pivot location 24. A second linkage 26 is pivotally connected to displaceable element 16 at a pivot joint 28 and pivotally associated with the base at a second displaceable pivot location 30. An actuation arrangement, described below in more detail, is associated with base 12 and is operable to act on first and second linkages 20, 26 so as to move the displaceable pivot locations 24 and 30, thereby adjusting a spacing and/or angle between the first and second contact surfaces 14 and 18.

Figure 2A:
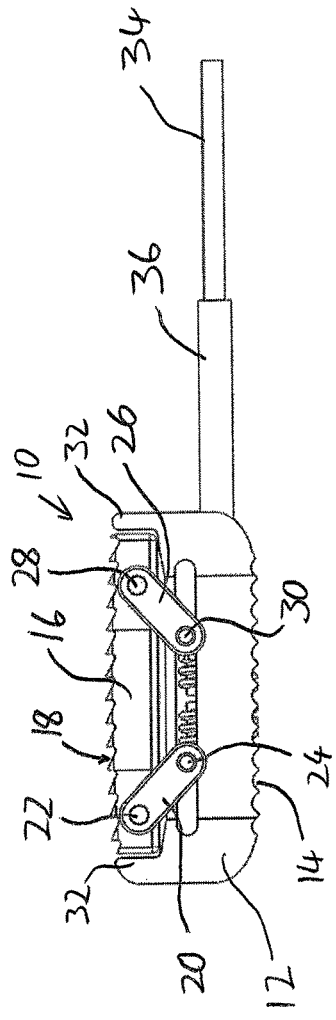
FIGS. 2A-2C are side, isometric and cutaway (along a center-plane of the implant) views, respectively, of the implant of FIG. 1A in a flat configuration with an adjustment tool attached.
Figure 2B:
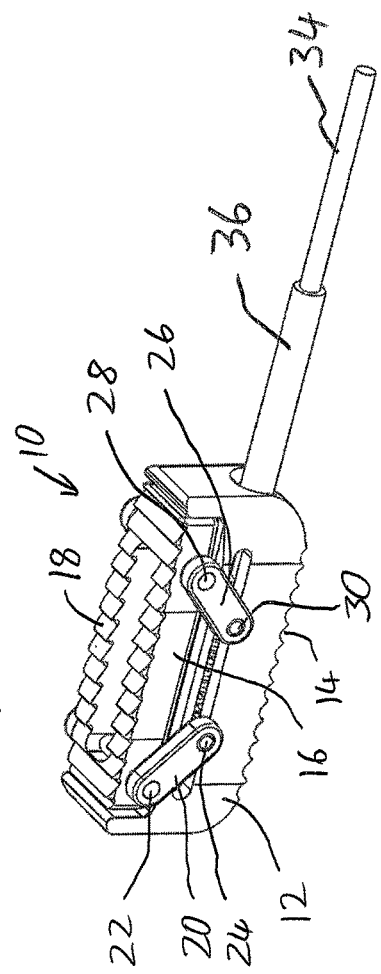
Figure 2C:
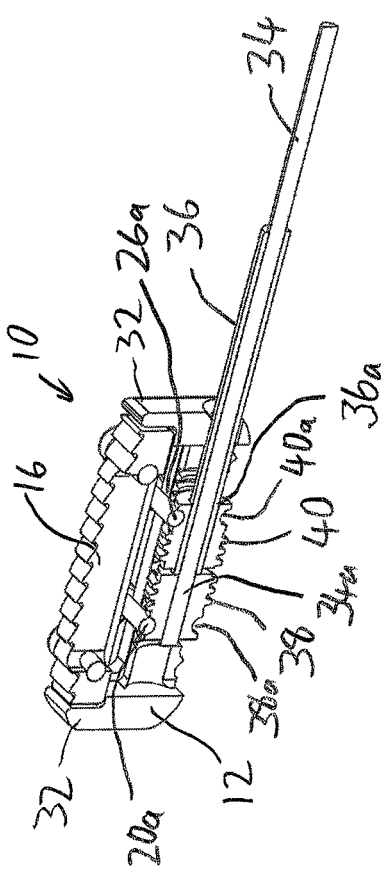
Figure 3A:
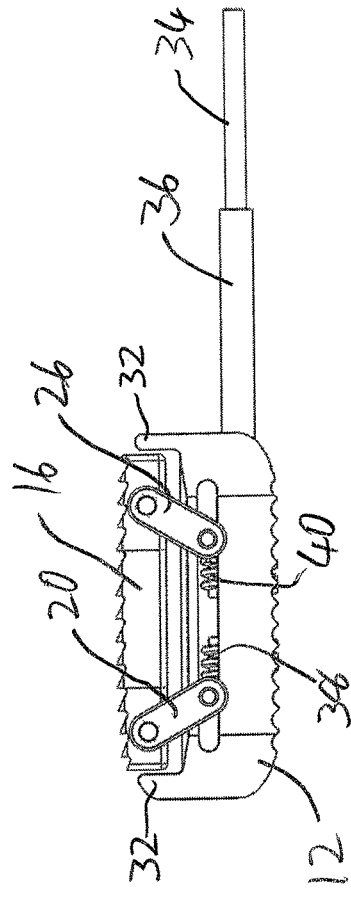
FIGS. 3A-3C are views similar to FIGS. 2A-2C, respectively, showing the implant in an intermediate, expanded configuration with the adjustment tool attached.
Figure 3B:
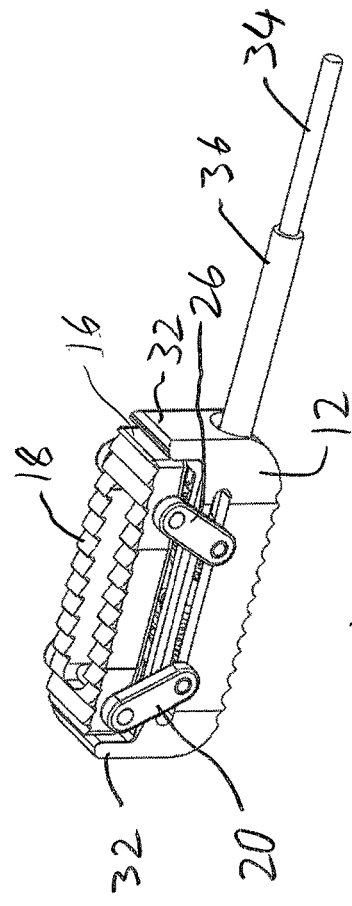
Figure 3C:
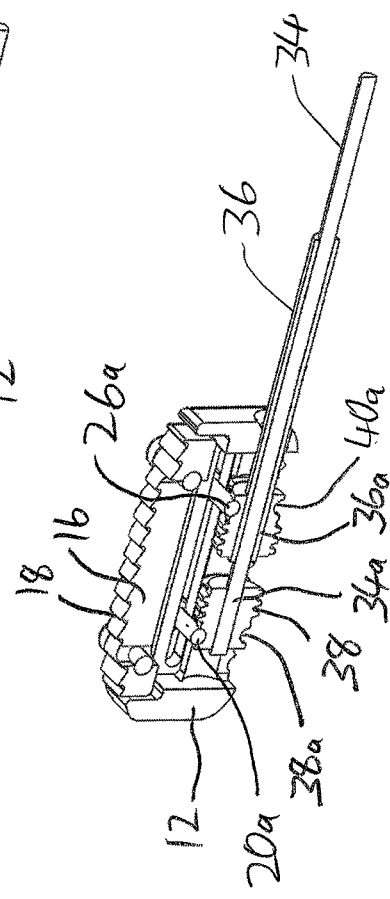
Figure 4A:
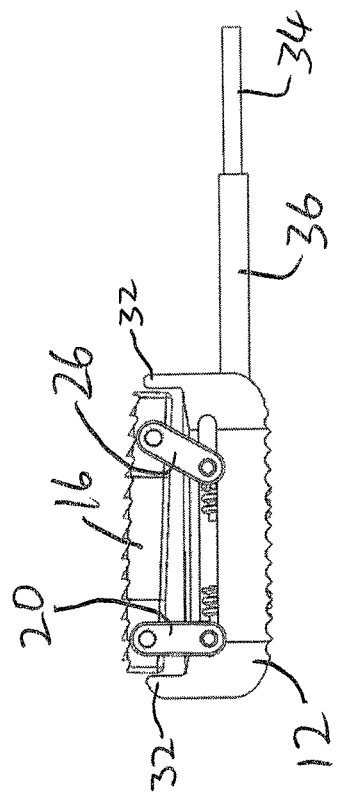
FIGS. 4A-4C are views similar to FIGS. 2A-2C, respectively, showing the implant in an intermediate, expanded and angled configuration with the adjustment tool attached.
Figure 4B:
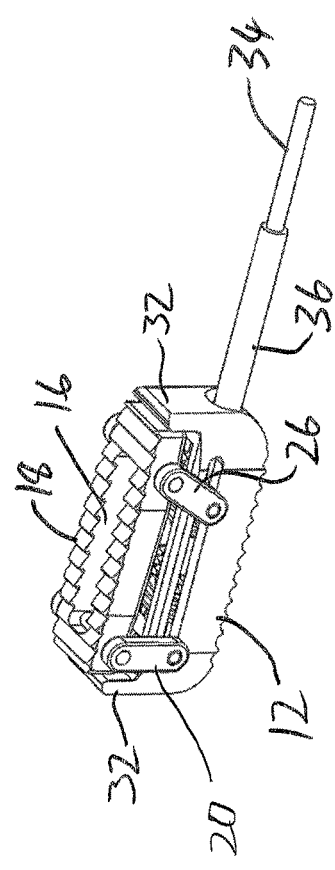
Figure 4C:
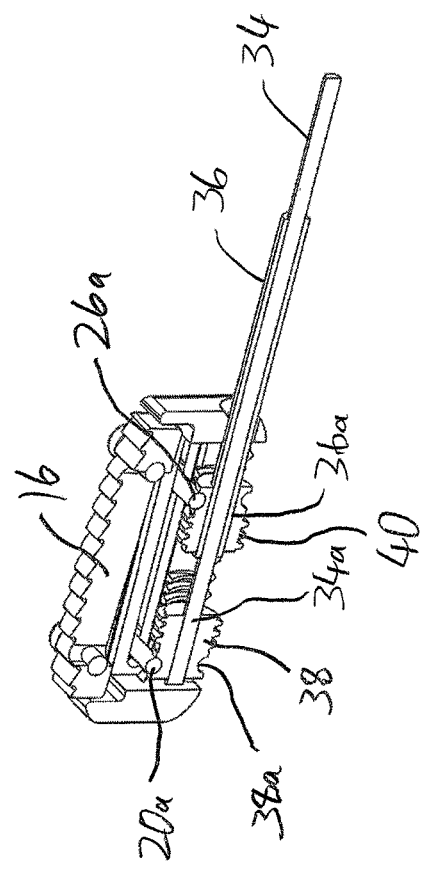
Figure 5:
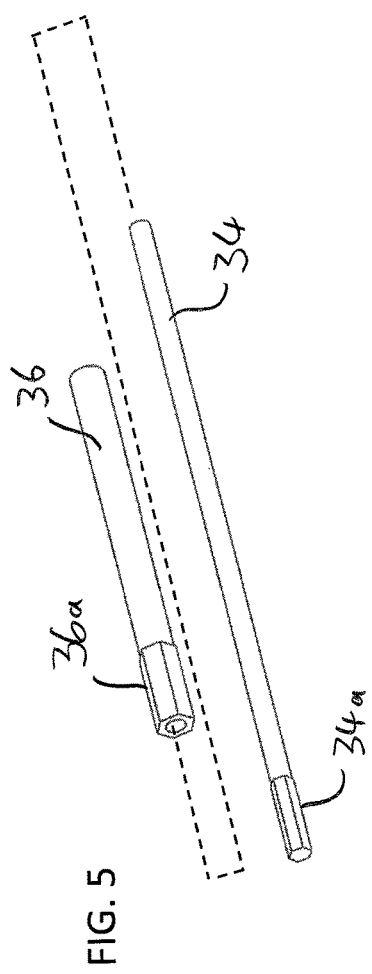
FIG. 5 is an isometric view of an embodiment of the adjustment tool used for rotating proximal and distal bolts of the implant to adjust the expansion and angle of the implant.
Figure 6:
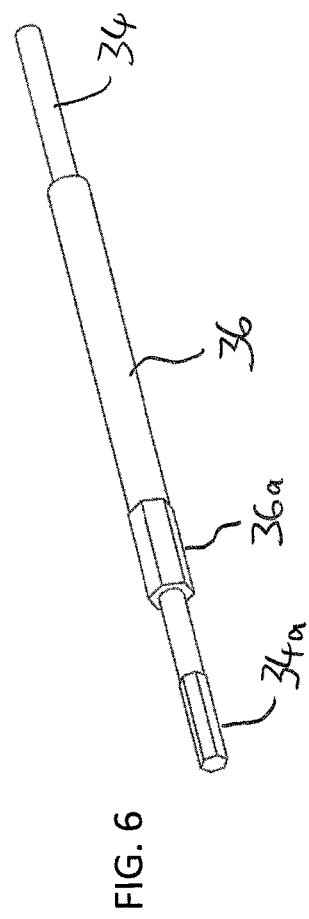
FIG. 6 is an isometric view of the adjustment tool of FIG. 5 assembled.
Figure 10A:
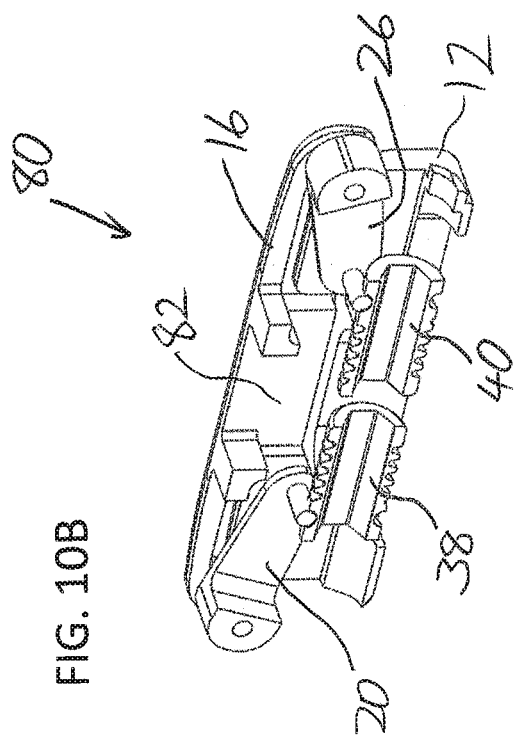
FIGS. 10A and 10B are isometric and cutaway (along a center-plane of the implant) views, respectively, of a variant of the implant of FIG. 1A-4C where the upper displaceable element has a length greater than a length of the base, the implant shown in a minimum height configuration.
Figure 10B:
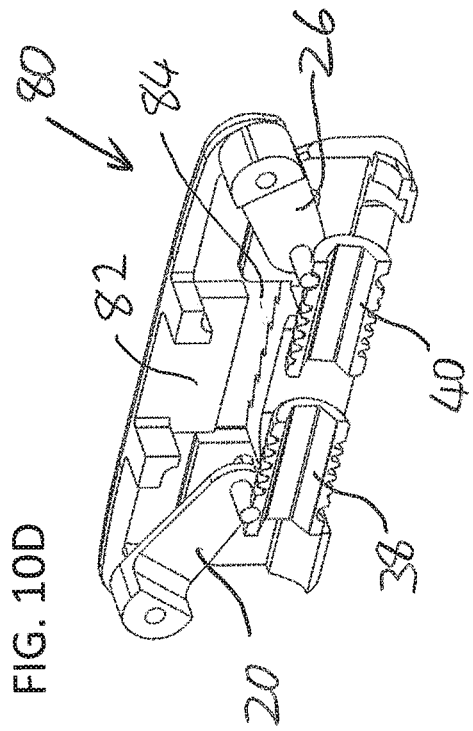
Figure 10C:
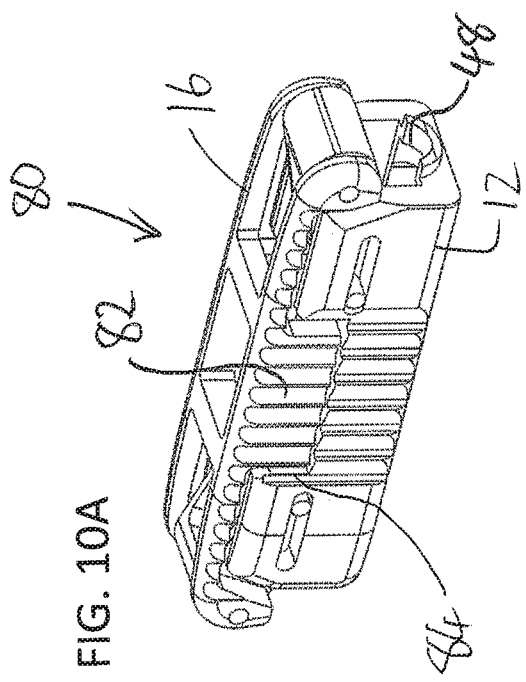
FIGS. 10C and 10D are views similar to FIGS. 10A and 10B, respectively, showing the implant in an expanded configuration.
Figure 10D:
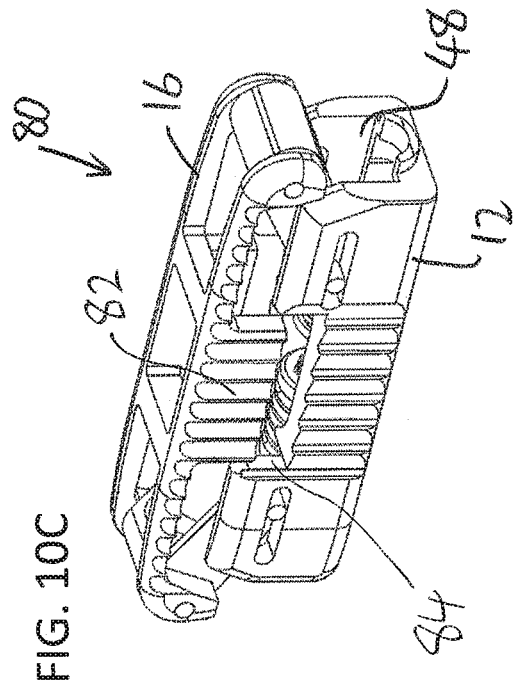

In certain particularly preferred but non-limiting implementations of the present invention as illustrated here, the actuation arrangement is selectively operable to adjust first displaceable pivot location 24 without moving second displaceable pivot location 30, or vice versa, thereby allowing control of both the spacing and the angular relationship between contact surfaces 14 and 18. Thus, for example, FIGS. 2A-2C illustrate a fully lowered state (i.e., with displaceable element 16 fully lowered, corresponding to a minimum spacing between the contact surfaces), in a state suitable for insertion of the implant into a body. FIGS. 3A-3C illustrate a state in which displaceable pivot locations 24 and 30 have been displaced apart along part of their ranges of motion, causing parallel lifting of displaceable element 16 relative to base 12 so as to increase the height/spacing. FIGS. 4A-4C illustrate a state where displaceable pivot location 30 remains in the same position as in FIGS. 3A-3C, but displaceable pivot location 24 has been further displaced, thereby raising one end of displaceable element 16 more than the other so as to produce an inclination of contact surface 18 relative to contact surface 14. The ability to provide controlled adjustment of both spacing and angle in a single product is particularly advantageous, for example, allowing controlled restoration of intervertebral space together with controlled restoration of lordosis and/or correction of scoliosis in a single procedure.

Parenthetically, it should be noted that terminology such as "up", "down", "raised", "lowered" and the like are used herein for simplicity of presentation in their intuitive sense when relating to the "base" being at the bottom of the displaceable element being at the top. This terminology in no way limits the intended orientation in which the product is to be used in practice, which will vary according to the details of each intended application.

As can be seen in FIGS. 2A, 3A and 4A, the preferred geometry of this embodiment is a quadrilateral defined by the pivot axes of connections 22, 28, 24 and 30, and where the segment parallel to the length of base 12 is elongated in order to expand or adjust the angle of the device. Thus, increasing a spacing between the first and second displaceable pivot locations 24 and 30 is effective to increase a spacing between first contact surface 14 and at least part of second contact surface 18. In order to implement this geometry, the locations of pivotal connections 22 and 28 are preferably near the ends of displaceable element 16, for example, with the axis of pivotal connection 22 with the distal-most 20% of a length of displaceable element 16 and with the axis of pivotal connection 28 within the proximal-most 20% of the length of displaceable element 16.

Linkages 20 and 26 preferably do not cross over each other, and are preferably not mechanically interconnected other than via base 12 and displaceable element 16. A quadrilateral geometry with four pivot axes is not inherently a rigid structure and could potentially allow displaceable element 16 to rock in a direction parallel to the length of base 12. To prevent or limit such motion, the various two-linkage embodiments described herein preferably have base 12 and displaceable element 16 formed with interlocking features deployed to limit motion of displaceable element 16 relative to base 12 in a direction parallel to the length of the base while allowing a range of spacing between the first and second contact surfaces. In the example illustrated here, base 12 is formed with end walls 32 which limit any such rocking motion to minimal levels. Alternative implementations of interlocking features performing this function are illustrated in the embodiments of FIGS. 10A-10D, which employs interlocking sidewall portions, and FIGS. 12A-12D which uses a dedicated anchoring tooth engaged in a corresponding channel. These various solutions may be used interchangeably between the various embodiments described herein.

Various particularly preferred implementations of the present invention use a threaded actuation arrangement to adjust the implant. Where independent control is desired for two linkages, a particularly compact and convenient form of actuation arrangement employs an actuator rod 34 mechanically associated with first linkage 20 such that rotation of the actuator rod displaces the first displaceable pivot location 24, and an actuator tube 36, deployed around actuator rod 34, mechanically associated with second linkage 26 such that rotation of the actuator tube displaces the second displaceable pivot location 30. A wide range of implementations of such threaded actuation arrangements fall within the scope of the present invention, including cases in which actuator tube 36 is linked via threaded engagement to base 12 and actuator rod 34 is linked via threaded engagement to actuator tube 36. In such a case, rotation of actuator tube 36 can directly generate displacement to move second linkage 26 and rotation of actuator rod 34 can generate displacement to move first linkage 20.

An alternative preferred implementation of a threaded actuation arrangement is illustrated in the embodiment of FIGS. 1A-7D. In this case, first and second linkage movers 38 and 40, engaged with base 12, are associated with linkages 20 and 26, respectively, so as to define displaceable pivot locations 24 and 30. In the preferred implementation illustrated here, each linkage mover 38, 40 is implemented as a threaded segment which engages a corresponding internally threaded track 42, 44 each extending along part of the length of base 12. By rotating each threaded segment about its central axis, the linkage mover is made to advance along the corresponding threaded track, thereby displacing the corresponding displaceable pivot location.

In this context, the term "threaded segment" is used to refer to a section of headless bolt which, when engaged in a female thread, can travel along that thread when rotated. The term "threaded track" is used to refer to any arrangement for receiving such a threaded segment in threaded engagement such that rotation of the threaded segment about its axis generates displacement along the axial direction. In cases where the implant structure is desired to be an open hollow structure, the threaded track is preferably formed by two or more strips, each formed with a partial thread, which extend along opposite sides of the implant. For positive retention of the threaded segments, it may be preferable for the threaded strips to leave gaps of less than 180 degrees around the periphery of the threaded segment. In this case, the threaded segments are preferably inserted during assembly of the implant, for example, from two halves or by addition of a threaded track cover element. Alternatively, the threaded track may have 180 degrees open for insertion of the threaded segment, and the segments may be held in place by engagement of a pin of the corresponding linkage.

In the preferred implementation illustrated here, engagement between each linkage 20, 26 and the corresponding linkage mover 38, 40 is achieved by a transverse pivot pin 20a, 26a of the linkage engaging an annular groove 38a, 40a of the linkage mover. The annular groove may be located at a distal or proximal end of the linkage mover, or at an intermediate position, subdividing the thread into two regions.

In order to maintain stability of linkages 20, 26 and ensure that engagement is maintained with the corresponding annular groove 38a, 40a, base 12 is preferably formed with a slot, or pair of slots 46, extending parallel to the length of base 12, in which pivot pins 20a and 26a are slidingly engaged. Slots 46 together with grooves 38a and 40a together effectively define the displaceable pivot locations 24 and 30 within which pivot pins 20a and 26a are retained. Linkages 20 and 26 are preferably implemented as a pair of parallel arms attached symmetrically to the ends of the pivot pins. The distances between pivot locations 24 or 30 and the pivotal connections to the displaceable element at 22 and 28, respectively, preferably correspond to the majority, and typically more than 80 percent, of the length of the arms of the linkages.

Each linkage mover 38, 40 preferably features a central non-circular opening, such as the hexagonal sockets 38b, 40b visible in FIG. 1A, which are preferably implemented as through-bores extending through the entire element. To facilitate adjustment of the implant after insertion into the body, base 12 preferably has an opening 48 for insertion of actuator rod 34 and actuator tube 36, each formed with a corresponding key configuration 34a, 36a for engaging the non-circular openings. It will be noted that socket 38b and the corresponding key configuration 34a are sized to be sufficiently smaller than socket 40b so that key configuration 34a can be inserted through the bore forming socket 40b to reach linkage mover 38. Once both keys are engaged, rotation of one or both of actuator rod 34 and actuator tube 36 result in corresponding rotation of the linkage movers about their central axis, and corresponding adjustment of the implant.

In certain particularly preferred implementations, first and second internally threaded tracks 42 and 44, and of course their corresponding threaded segments 38 and 40, are implemented with opposite thread directions. In the example illustrated here, threaded track 42 and segment 38 have right-handed thread while threaded track 44 and segment 40 have left-handed thread. As a result, for parallel lifting of displaceable element 16, rotation of actuator rod 34 and actuator tube 36 in the same direction results in opposing displacements of the first and second displaceable pivot locations, corresponding to parallel lifting/lowering of displaceable element 16. Where angular adjustment of the upper contact surface is required, one of the actuator elements is then rotated without the other.

Parenthetically, although described thus far in a preferred embodiment which allows separate adjustment of each linkage, in certain cases where only one degree of freedom of adjustment is required, a simplified structure may employ a single elongated actuator rod (not shown) rotationally engaged with both threaded segments 38 and 40 such that rotation of the elongated actuator rod is effective to displace the displaceable pivot locations of first and second linkages 20, 26 in opposing directions. Depending upon the lengths of the linkages and the pitches of the threading, the displacement may be pure parallel displacement of the contact surfaces or some predefined combination of lifting and tilting according to the desired motion profile for a given application.

After the desired deployment and adjustment of the implant, the actuator elements are withdrawn leaving the adjusted implant in place within the body. The pitch of the threaded engagement is such that the state of the implant remains frictionally locked and can function as a load bearing structure. If repositioning or removal is required, the actuator elements may be reinserted to allow lowering of the displaceable element for removal or repositioning. Depending on the intended application, the implant can then be filled with bone or bone-growth enhancing material, or any other filler suited to the particular application. For fusion applications, the presence of bone windows in each contact surface and the mainly empty inner volume of the implant facilitate rapid formation of a bone bridge through the implant.

Turning now to FIGS. 8A-8D, there is shown a variant embodiment of an adjustable implant, generally designated 60, according to an aspect of the present invention. Implant 60 is generally similar to implant 10 described above, and equivalent elements are labeled similarly. Implant 60 differs primarily in that displaceable element 16 is here pivotally connected to base 12 at a pivot joint 62 and only a single pivotal linkage 20, linkage mover 38 and threaded track 42 are provided. Displacement of linkage mover 38 results in a change of angle of second contact surface 18 relative to first contact surface 14. This implementation is particularly suitable for spinal fusion applications with correction of lordotic angle, or for correction of scoliosis. Optionally, linkage 20 may be made longer and threaded track 42 may extend along a majority of a length of base 12, thereby providing large angle adjustments suitable for hyperlordotic applications. In all other respects, the structure and function of implant 60 may be fully understood by analogy to the description of implant 10 above.

Turning now to FIGS. 9A-9C, this shows an adjustable implant, generally designated 70, which is structurally and functionally equivalent to implant 10 described above. Implant 70 differs from implant 10 in that linkages 20 and 26 are here deployed internally to the sidewall of base 12. In certain cases this may be advantageous, for example, providing a smoother outer profile in the case that the implant is to be inserted by sliding through an undersized tissue aperture.

Turning now to FIGS. 10A-10D, these illustrate an adjustable implant, generally designated 80, which is structurally and functionally analogous to implant 10, but which has a displaceable element 16 of length greater than the length of base 12. The use of a longer displaceable element precludes the use of end walls 32 to limit racking motion. Accordingly, an alternative form of engagement between displaceable element 16 and base 12 if provided in the form of a downward projecting sidewall portion 82 projecting downwards as shown from displaceable element 16 so as to interengage with a corresponding sidewall cutout 84 in the wall of base 12. This configuration allows height adjustment by lifting of displaceable element 16 relative to base 12 while limiting rocking motion of displaceable element 16 parallel to the length of base 12. For implementations with separately adjustable linkages, the clearance provided by cutout 84 is made sufficient to also accommodate the available range of tilting motion.

Figure 11A:
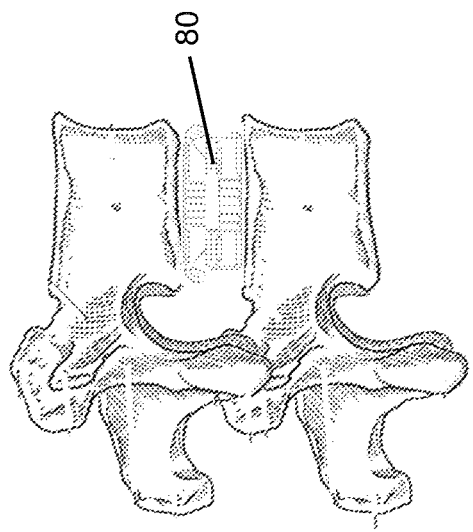
FIGS. 11A and 11B are side views of the implant of FIG. 10A, located between two vertebra in a minimum height and a vertically expanded state, respectively.
Figure 11B:
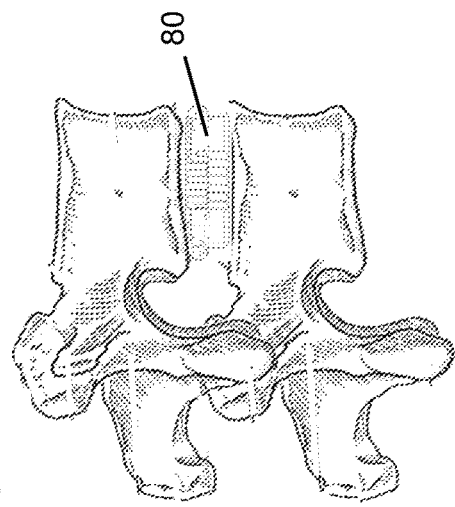
Figure 11C:
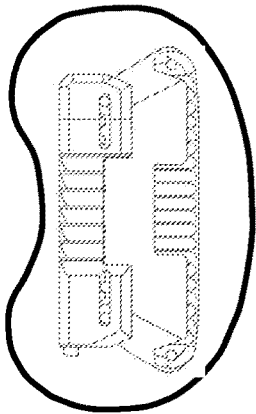
Figure 11D:
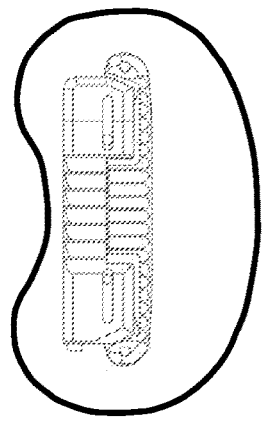

As mentioned above, the implants of the present invention may be used for a wide range of application. By way of non-limiting example, FIGS. 11A and 11B illustrate the use of implant 80 in a "vertical" orientation to achieve intervertebral spacing restoration as part of a fusion procedure, before and after actuation to restore the spacing. FIGS. 11C and 11D illustrate use of implant 80 with a transverse approach to open in an "axial" plane, thereby providing support over a large region of the vertebral endplate via a relatively small incision, as part of an alternative fusion protocol. These and many other suitable applications of the adjustable implants of the present invention will be fully understood by a person having ordinary skill in the art.

Figures 12A, 12B, 12C:
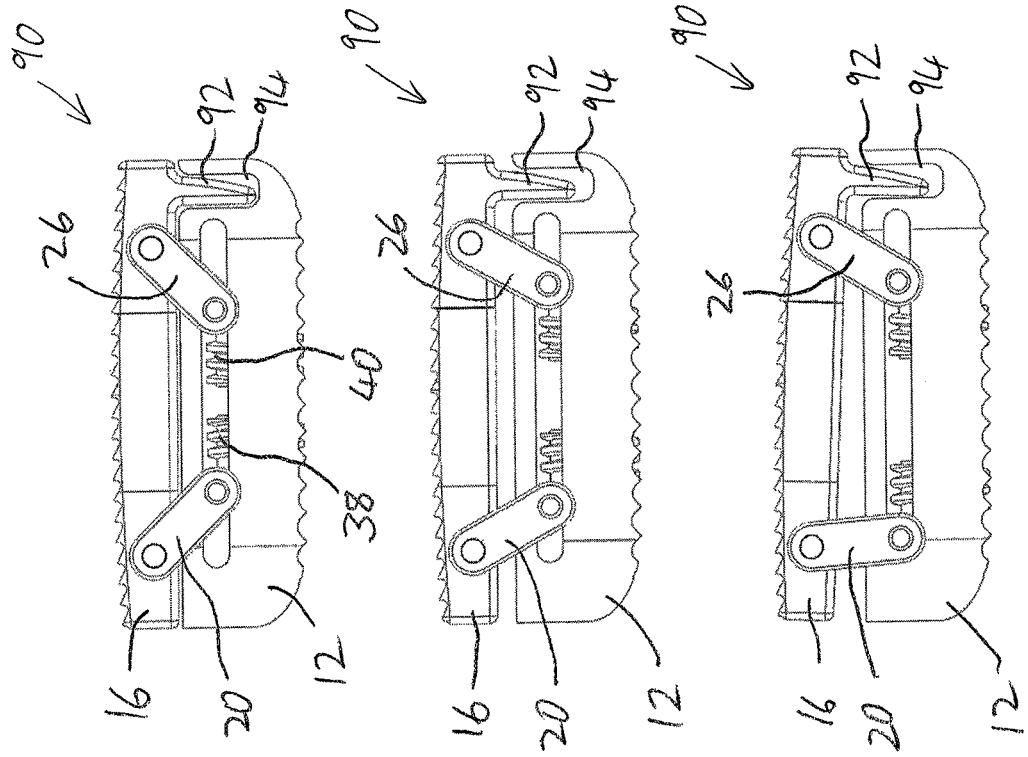
FIGS. 12A-12C are side views of a variant of the implant of FIG. 1A-4C, illustrating a form of interengagement between a displaceable element and a base, the implant being shown in a minimum height state, an expanded state and an expanded and angled state, respectively.

Turning finally to FIGS. 12A-12C, these illustrate a further adjustable implant, generally designated 90, which is generally structurally and functionally analogous to implant 10, but employs an alternative interengagement between displaceable element 16 and base 12 to limit rocking motion.

In this case, a dedicated anchoring tooth 92 projecting downwards from displaceable element 16 is engaged in a corresponding channel 94 in base 12. The tooth and/or the channel may be shaped in order to accommodate the achievable range of elevation and tilt so as to maintain sufficient engagement to limit longitudinal rocking without limiting the intended range of motion. The tooth and channel engagement is typically implemented symmetrically on both sides of the central axis of the implant, and may be implemented anywhere along the length of the implant, and at one or more locations along that length. In all other respects, the structure and function of implant 90 will be fully understood by analogy to the description of implant 10 above.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. An adjustable implant for deployment between a first and a second tissue surface, the implant comprising:
   (a) a base having a length, said base providing a first contact surface for deployment against the first tissue surface;
   (b) a displaceable element providing a second contact surface for deployment against the second tissue surface;
   (c) a linkage pivotally connected to said displaceable element; and
   (d) a linkage mover engaged with said base so as to be displaceable along at least part of said length of said base, said linkage mover being associated with said linkage so as to define a displaceable pivot location for pivotal motion of said linkage relative to said base,
   wherein said base comprises an internally threaded track, and wherein said linkage mover comprises a threaded segment engaged with said internally threaded track such that rotation of said threaded segment about a central axis of said threaded segment advances said linkage mover along said threaded track, thereby displacing said displaceable pivot location such that said linkage adjusts a separation between said first contact surface and at least part of said second contact surface,
   wherein said linkage mover further comprises an annular groove circumscribing said central axis, and wherein said linkage comprises a pivot pin engaged in said annular groove so as to at least partially define said displaceable pivot location.

2. The adjustable implant of claim 1, wherein said base further comprises a slot extending parallel to said length, and wherein said pivot pin is slidingly engaged in said slot.

3. The adjustable implant of claim 1, wherein said linkage mover further comprises a central non-circular opening, and wherein said base has an opening for insertion of an actuator rod having a key configuration for engaging said non-circular opening so as to allow rotation of said linkage mover so as to adjust said implant.

4. The adjustable implant of claim 1, wherein said displaceable element is pivotally connected to said base such that displacement of said linkage mover results in a change of angle of said second contact surface relative to said first contact surface.

5. The adjustable implant of claim 1, wherein said linkage is a first linkage and said linkage mover is a first linkage mover, the adjustable implant further comprising:
   (a) a second linkage pivotally connected to said displaceable element; and
   (b) a second linkage mover engaged with said base so as to be displaceable along part of said length of said base, said second linkage mover being associated with said second linkage so as to define a displaceable pivot location for pivotal motion of said second linkage relative to said base.

6. The adjustable implant of claim 5, wherein said internally threaded track is a first internally threaded track extending along only part of said length, and wherein said base further comprises a second internally threaded track extending along a second part of said length, said second linkage mover comprising a threaded segment engaged with said second internally threaded track, said first and second internally threaded tracks having opposite thread directions.

7. The adjustable implant of claim 6, further comprising an elongated actuator rod rotationally engaged with both said threaded segments of both said first and second linkage movers such that rotation of said elongated actuator rod is effective to displace said displaceable pivot locations of said first and second linkages in opposing directions.

8. The adjustable implant of claim 6, further comprising:
   (a) an actuator rod passing through said threaded segment of said second linkage mover and rotationally engaged with said threaded segment of said first linkage mover; and
   (b) an actuator tube deployed around said actuator rod, said actuator tube being rotationally engaged with said threaded segment of said second linkage mover.

9. The adjustable implant of claim 5, wherein said first and second linkages are deployed such that increasing a spacing between said first and second displaceable pivot locations is effective to increase a spacing between said first and second contact surfaces.

10. The adjustable implant of claim 5, wherein said base and said displaceable element are formed with interlocking features deployed to limit motion of said displaceable element relative to said base in a direction parallel to said length while allowing a range of spacing between said first and second contact surfaces.

11. An adjustable implant for deployment between a first and a second tissue surface, the implant comprising:
   (a) a base having a length, said base providing a first contact surface for deployment against the first tissue surface;
   (b) a displaceable element providing a second contact surface for deployment against the second tissue surface;
   (c) a first linkage pivotally connected to said displaceable element and pivotally associated with said base at a first displaceable pivot location;
   (d) a second linkage pivotally connected to said displaceable element and pivotally associated with said base at a second displaceable pivot location; and
   (e) an actuation arrangement associated with said base and operable to act on said first and second linkages so as to move said displaceable pivot locations, thereby adjusting a spacing and/or angle between said first and second contact surfaces, said actuation arrangement being selectively operable to adjust said first displaceable pivot location without moving said second displaceable pivot location.

12. The adjustable implant of claim 11, wherein said first and second linkages are deployed such that increasing a spacing between said first and second displaceable pivot locations is effective to increase a spacing between said first and second contact surfaces.

13. The adjustable implant of claim 11, wherein said actuation arrangement is a threaded actuation arrangement comprising:
   (a) an actuator rod mechanically associated with said first linkage such that rotation of said actuator rod displaces the first displaceable pivot location; and
   (b) an actuator tube deployed around said actuator rod, said actuator tube being mechanically associated with said second linkage such that rotation of said actuator tube displaces the second displaceable pivot location.

14. The adjustable implant of claim 13, wherein said threaded actuation arrangement is configured such that rotation of said actuator rod and said actuator tube in the same direction results in opposing displacements of said first and second displaceable pivot locations.

15. The adjustable implant of claim 11, wherein said base and said displaceable element are formed with interlocking features deployed to limit motion of said displaceable element relative to said base in a direction parallel to said length while allowing a range of spacing between said first and second contact surfaces.

16. An adjustable implant for deployment between a first and a second tissue surface, the implant comprising:
   (a) a base having a length, said base providing a first contact surface for deployment against the first tissue surface;
   (b) a displaceable element providing a second contact surface for deployment against the second tissue surface;
   (c) a first linkage having a mechanical interconnection with said displaceable element and a mechanical interconnection with said base, at least one of said mechanical interconnections being a pivotal interconnection, said first linkage extending in a first direction of extension;
   (d) a second linkage having a mechanical interconnection with said displaceable element and a mechanical interconnection with said base, at least one of said mechanical interconnections being a pivotal interconnection, said second linkage extending in a second direction of extension; and
   (e) an actuation arrangement associated with said base and operable to act on said first and second linkages so as to change an angle of said first and second directions of extension relative to said length of said base, thereby adjusting a spacing and/or angle between said first and second contact surfaces, said actuation arrangement being selectively operable to change said angle of said first direction of extension without changing said angle of said second direction of extension.

* * * * *